United States Patent [19]

Spivack

[11] 4,163,006
[45] Jul. 31, 1979

[54] COMPOSITIONS STABILIZED WITH POLYALKYLTHIOBENZENES

[75] Inventor: John D. Spivack, Spring Valley, N.Y.

[73] Assignee: Ciba-Geigy Corporation, Ardsley, N.Y.

[21] Appl. No.: 795,269

[22] Filed: May 9, 1977

[51] Int. Cl.² .................. C08K 5/37; C10M 1/38; C10M 1/42
[52] U.S. Cl. .................. 260/45.8 NT; 106/169; 106/270; 260/398.5; 260/799; 252/45; 260/45.7 S; 260/45.85 B; 260/45.9 NC; 260/45.95 R; 260/45.95 D
[58] Field of Search .................. 260/45.7 S, 45.95 C, 260/45.95 G; 252/45; 526/57

[56] References Cited

U.S. PATENT DOCUMENTS

| | | | |
|---|---|---|---|
| 2,472,318 | 6/1949 | Subkow | 252/45 |
| 3,228,989 | 1/1966 | Reifschneider | 260/609 E |
| 3,258,449 | 6/1966 | Heuck et al. | 260/45.7 S |
| 3,293,209 | 12/1966 | Baldwin et al. | 260/45.7 S |
| 3,502,613 | 3/1970 | Berger | 260/45.8 NT |
| 3,506,608 | 4/1970 | Braus et al. | 260/45.7 S |
| 3,637,582 | 1/1972 | Gilles | 260/45.8 NT |
| 3,652,680 | 3/1972 | Buchholz | 260/45.7 S |
| 3,876,613 | 4/1975 | Needham et al. | 526/57 |
| 3,974,132 | 8/1976 | Valdiserri | 526/57 |
| 4,028,332 | 6/1977 | Needham et al. | 260/45.95 C |

Primary Examiner—Hosea E. Taylor
Assistant Examiner—R. A. White
Attorney, Agent, or Firm—Vincent J. Cavalieri

[57] ABSTRACT

Organic materials are stabilized against oxidative and ultraviolet light degradation by incorporating therein polyalkylthiobenzenes having the formula

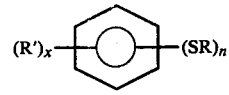

wherein R is alkyl or cycloalkyl, R' is alkyl, n is 2 to 6 and x is 0 to 4, provided that n+x is not greater than 6.

10 Claims, No Drawings

COMPOSITIONS STABILIZED WITH POLYALKYLTHIOBENZENES

BACKGROUND OF THE INVENTION

Organic polymeric materials are subject to thermal, oxidative and ultraviolet light degradation which exhibits itself in the loss of physical properties and in the change of color. Therefore it is generally necessary to incorporate into the polymeric materials stabilizers which retard their decomposition. A variety of compounds have been employed for that purpose, the most widely used being hindered-phenolic alkanoates.

It has now been found that the polyalkylthiobenzenes of this invention are exceptionally good stabilizers against thermal and oxidative degradation. These compounds belong to a generally known class of aromatic thioethers as disclosed in Adams et al, J. Am. Chem. Soc. 81, 4927 (1959) and in U.S. Pat. Nos. 3,100,802 and 3,228,989. However the use of polyalkylthiobenzenes as stabilizers of organic substances has not been taught by the prior art. The most related class of compounds that have been used as stabilizers are polyphenyl thioethers disclosed in U.S. Pat. No. 3,647,752 and polyphenyl and polyalkyl thioethers disclosed in U.S. Pat. No. 3,751,358. Such compounds differ substantially from those of the present invention because they do not have thioalkyl groups substituted on the aromatic ring. British Pat. No. 951,933 disclose diphenylthioethers where the phenyl groups are substituted with hydroxyl and alkyl groups. The most relevant prior art might be U.S. Pat. Nos. 3,076,851 and 3,084,196 which disclose thiophenols where the benzene ring is substituted with one thioalkyl and one alkyl group. These compounds are said to be useful as antioxidant lubricating oil additives. The compounds of this invention may or may not have alkyl substituents and they carry at least two thioalkyl groups. Such compounds are substantially more efficient stabilizers, especially in crosslinked polyolefins.

DETAILED DISCLOSURE

This invention is directed to polymeric compositions subject to oxidative and ultraviolet light degradation stabilized with a polyalkylthiobenzene and to a method of stabilizing such polymeric materials with said compounds. More specifically, this invention deals with the stabilization of polymeric materials with polyalkylthiobenzenes having the formula

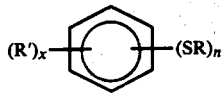

wherein
R is an alkyl group of 1 to 24 carbon atoms, a cycloalkyl group of 4 to 7 carbon atoms or an alkylcycloalkyl group of 7 to 30 carbon atoms,
R' is an alkyl group of 1 to 18 carbon atoms,
n is an integer from 2 to 6, and
x is an integer from 0 to 4 provided that n n+x is not greater than 6.

Preferably the group R is an alkyl group of 2 to 18 carbon atoms and most preferably it is an alkyl group of 8 to 12 carbon atoms. Said group can therefore be methyl, ethyl, propyl, isopropyl, various straight chain and branched chain butyl, pentyl, hexyl, heptyl octyl, dodecyl, hexadecyl, octadecyl and the like. When R is cycloalkyl it can be cyclobutyl, cyclopentyl, cyclohexyl or cycloheptyl unsubstituted or substituted with alkyl groups preferably 1 to 3 alkyl groups, having 1 to 8 carbon atoms, especially 1 to 4 carbons.

The group R' is preferably an alkyl of 1 to 8 carbon atoms and most preferably 1 to 4 carbon atoms.

The stabilizers of this invention can be polyalkylthiobenzenes where the benzene ring contains no further substituents or polyalkylthiobenzenes where the benzene ring is further substituted with up to four alkyl groups. Thus in the stabilizers of this invention n is an integer of 2 to 6, preferably 2 to 5 and most preferably 2 to 4. Correspondingly x is 0 to 4, preferably 0 to 3.

The above mentioned stabilizers can be prepared by known methods. The preferred method may be represented by the following equations:

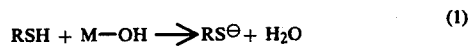  (1)

  +

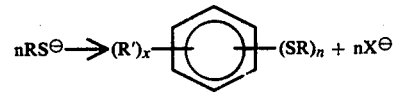  (2)

where R, R', n and 1 are as defined above, X is a halogen, usually chlorine and M is an alkali or alkaline earth metal, usually sodium or potassium.

Reaction (2) is usually carried out in a solvent such as alcohols, polar aprotic solvents, tetrahydrofuran, methyl-, ethyl-, propyl-, and butyl- cellosolve, N-alkyl pyrrolidinones and dimethylsulfoxide. The preferred solvents are non-polar aprotic solvents such as dimethylacetamide, dimethylformide, N-methylpyrrolidinone. The most preferred solvents are dimethylacetamide and dimethylformamide. Reaction (2) can be carried out at temperatures from about 80° C. to reflux temperature of the reaction mixture. The temperature range used for the most preferred solvents is 100° C. to the reflux temperature of the reaction mixture.

As previously stated, the compounds of the present invention are useful in the stabilization of organic material normally subject to deterioration. Organic materials such as, for example, the following polymers, can be stabilized using the compounds of the formula I.

1. Polymers which are derived from hydrocarbons with single or double unsaturation, such as polyolefins, for example, polyethylene, which can optionally be crosslinked, polypropylene, polyisobutylene, polymethylbutene-1, polymethylpentene-1, polybutene-1, polyisoprene, polybutadiene, polystyrene, polyisobutylene, copolymers of the monomers on which the homopolymers mentioned are based, such as ethylene propylene copolymers, propylene-butene-1 copolymers, propylene-isobutene copolymers, styrene-butadiene copolymers and terpolymers of ethylene and propylene with a diene, such as, for example, hexadiene, dicyclopentadiene or ethylidenenorbornene; mixtures of above mentioned homopolymers, such as for example, mixtures of polypropylene and polyethylene, polypropylene and polybutene-1, or polypropylene and polyisobutylene or chlorinated polyolefins.

2. Vinyl polymers containing halogen, such as polyvinyl chloride, polyvinylidene chloride, polyvinyl fluoride, but also polychloroprene and chlorinated rubbers.

3. Polymers which are derived from α,β-unsaturated acids and their derivatives, such as polyacrylates and polymethacrylates, polyacrylamides and polyacrylonitrile, as well as their copolymers with other vinyl compounds, such as acrylonitrile/butadiene/styrene, acrylonitrile/styrene and acrylonitrile/styrene/acrylic ester copolymers.

4. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers.

6. Polyacetals, such as polyoxymethylene and polyoxyethylene, as well as those polyoxymethylenes which contain ethylene oxide as the comonomer.

7. Polyphenylene oxides.

8. Polyurethanes and polyureas.

9. Polycarbonates.

10. Polysulphones. propylene-isobutylene

11. Polyamides and copolyamides which are derived from diamines and dicarboxylic acids and/or from aminocarboxylic acids or the corresponding lactams, such as polyamide 6, polyamide 6/6, polyamide 6/10, polyamide 11 and polyamide 12.

12. Polyesters which are derived from dicarboxylic acids and dialcohols and/or from hydroxycarboxylic acids or the corresponding lactones, such as polyethylene glycol terephthalate or poly-14-dimethylolcyclohexane terephthalate.

13. Crosslinked polymers which are derived from aldehydes on the one hand and phenols, ureas and melamines on the other, such as phenol-formaldehyde, urea-formaldehyde and melamine-formaldehyde resins.

14. Alkyd resins, such as glycerine-phthalic acid resins and their mixtures with melamine-formaldehyde resins.

15. Unsaturated polyester resins which are derived from copolyesters of saturated and unsaturated dicarboxylic acids with polyhydric alcohols, with vinyl compounds as crosslinking agents, and also their halogen-containing modifications of low inflammability.

16. Natural polymers such as cellulose, rubber, proteins and their polymer-homologously chemically modified derivatives, such as cellulose acetates, cellulose proprionates and cellulose butyrates, or the cellulose ethers, such as methylcellulose.

17. High molecular monomeric substances, for example, mineral oils, animal and vegetable fats, oils and waxes, or oils, waxes and fats based on synthetic esters.

Other polymeric substrates in which the compounds of this invention are particularly useful are polystyrene, including impact polystyrene, ABS resin, SBR, polyisoprene, as well as natural rubber, polyesters including polyethylene terephthalate and polybutylene terephthalate, including copolymers.

The compounds of this invention are also particularly useful in stabilizing lubricating oils of various types including natural and synthetic hydrocarbon lubricating oils, particularly paraffinic lubricating oils, aliphatic esters, polyalkylene oxides, silicones, esters of phosphoric and silicic acids, highly fluorine-substituted hydrocarbons, and the like. Specifically, such aliphatic esters which are usefully stabilized comprise dihexyl acetate, di-(2-ethylhexyl)acelate, di-(3,5,5-trimethylhexyl)glutarate, di(3,5,5-trimethylpentyl)glutarate, di-(2-ethylhexyl)pimelate, di-(2-ethylhexyl)adipate, diisoamyl adipate, triamyl tricarballylate, pentaerythritol tetracaproate, dipropylene glycol dipelargonate, 1,5-pentanediol di-(2-ethylhexanoate), and the like. Other specific lubricants include polyisopropylene oxide, polyisopropylene oxide diether, polyisopropylene oxide diester, and the like, as well as methyl silicone, methylphenyl silicone, tetracosyl silicate, etc. and fluorinated oils, such as perfluorohydrocarbons.

The substrates which are especially well stabilized by polyalkylthiobenzenes are polyolefin homopolymers and polyolefin copolymers such as polypropylene, low and high density polyethylene, crosslinked low-density polyethylene, ethylenevinyl acetate copolymers and ethylene-ethyl acrylate copolymers ethylene-propylene-diene rubber (EPDM), polybutadiene, vulcanized and non-vulcanized SBR (styrene-butadiene rubber) acrylonitril-butadiene-styrene (ABS) copolymer, chlorinated olefins such as chlorinated polyethylene, polypropylene and polybutene, and polyolefin copolymers, lubricating oil and the like.

In order to attain the desired stabilization effectiveness the stabilizers are incorporated into the organic substrate by known methods in the amount of from 0.01 to 5% by weight and preferably from 0.05 to 1% by weight. Said compounds stabilize organic materials against degradation caused by oxidation and/or light. These stabilizers are particularly effective in stabilizing polyolefins, especially polypropylene and crosslinked polyethylene, as well as lubricating oils. For stabilizing polyolefins, especially polypropylene, it is preferable that n is 3 or higher.

Polyalkylthiobenzenes of this invention are particularly effective as stabilizers of crosslinked polyolefins. Antioxidants designed for the stabilization of crosslinked polyethylene, for example, chemically or radiation crosslinked polyethylene, preferably should possess the following properties:

(1) Provide effective inhibition against oxidation over long periods of time at both ambient and elevated temperatures.

(2) Have little, if any, tendency to exude to the surface of formulated low-density polyethylene both before and after curing, for example, by peroxides such as dicumyl peroxide.

(3) Show little tendency to discolor during use and storage because much of the crosslinked polyethylene is used in finished products which are either natural or light in color. Crosslinked polyethylene used in wire and cable insulation may be produced in a variety of colors providing an essential identification code for the various uses to which wire and cable is put.

The natural formulated polyethylene should be resistant to discoloration either due to the ingredients incorporated therein, including the antioxidant or due to the base resin. Obviously, discoloration due to oxidation is masked in black colored crosslinked polyethylen, such as carbon loaded polyethylene. In fact the compounds of this invention are very effective stabilizers of carbon filled polymers of many types. For illustrative purposes the following carbon black loaded polymers are highly stabilized with polyalkylthiobenzenes: polypropylene, low density polyethylene, cross-linked polyethylene ethylene-propylene copolymer, acrylonitrile-butadiene-styrene copolymer (ABS), pigmented nylon, polybutene, polyvinyl chloride, styrene-butadiene rubber (SBR), polybutadiene, polyisoprene, butyl rubber, chlorobutyl rubber, bromobutyl rubber, chlorosulfonated polyethylene (Hypalon), chlorinated polyethylene, carbon black and talc filled polypropylene and the like.

Although the polyalkylthiobenzenes of this invention can be used very effectively as the sole stabilizers, it is often more advantageous to use additional stabilizers to provide more complete stabilization under any circumstances. Such additional additives are phenolic antioxidants, phosphites, metal deactivators, thio-synergists and crosslinking agents.

Illustrative examples of phenolic antioxidants are:
1. Antioxidants
1.1. Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2. Derivatives of alkylated hydroquinones, such as, for example, 2,5-di-tert.-butyl-hydroquinone, 2,5-di-tert.-amyl-hydroquinone, 2,6-di-tert.-butyl-hydroquinone, 2,5-di-tert.-butyl-4-hydroxy-anisole, 3,5-di-tert.-butyl-4-hydroxyanisole, tris-(3,5-di-tert.-butyl-4-hydroxyphenyl)-phosphite, 3,5-di-tert.-butyl-4-hydroxyphenyl-stearate and bis-(3,5-di-tert.-butyl-4-hydroxyphenyl)-adipate.

1.3. Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl)-disulpfide.

1.4. Alkylidene-bisphenols, such as, for example 2,2'-methylene-bis-(6-tert.-butyl-4-methylphenol), 2,2'-methylene-bis-(6-tert.-butyl-4-ethylphenol), 4,4'-methylene-bis-(6-tert. butyl-2-methylphenol), 4,4'-methylene-bis-(2,6--di-tert.-butylphenol), 2,6-di-(3-tert.butyl-5-methyl-2-hydroxybenzyl)-4-methylphenol, 4-methylphenol, 2,2'-methylene-bis-[4-methyl-6-(α-methyl-cyclohexyl)-phenol], 1,1-bis(3,5-dimethyl-2-hydroxyphenyl)-butane, 1,1-bis-(5-tert.butyl-4-hydroxy-2-methylphenyl)-butane, 2,2-bis-(3,5-di-tert.-butyl-4-hydroxyphenyl)-propane, 1,1,3-tris-(5-tert.butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.butyl-4-hydroxy-2-methylphenyl)-pentane and ethylene glycol bis-[3,3-bis(3'-tert.butyl-4'-hydroxyphenyl)-butyrate].

1.5. O-, N- and S-benzyl compounds, such as, for example, 3,5,3',5'-tetra-tert.butyl-4,4'-dihydroxydibenzyl ether, 4-hydroxy-3,5-dimethylbenzyl-mercaptoacetic acid octadecyl ester, tris-(3,5-di-tert.butyl-4-hydroxybenzyl)-amine and bis-(4-tert.butyl-3-hydroxy-2,6-dimethylbenzyl)-dithioterephthalate.

1.6. Hydroxybenzylated malonic esters, such as, for example, 2,2-bis-(3,5-di-tert.butyl-2-hydroxybenzyl)-malonic acid dioctadecyl ester, 2-(3-tert.butyl-4-hydroxy-5-methyl-benzyl)-malonic acid dioctadecyl ester, 2,2-bis-(3,5-di-tert.butyl-4-hydroxybenzyl)-malonic acid didodecylmercaptoethyl ester and 2,2-bis(3,5-di-tert.butyl-4-hydroxybenzyl)-malonic acid di-[4-(1,1,3,3-tetramethylbutyl)-phenyl] ester.

1.7. Hydroxybenzyl-aromatics, such as, for example, 1,3,5-tri-(3,5-di-tert.butyl-4-hydroxybenzyl)-2,4,6-trimethylbenzene, 1,4-di-(3,5-di-tert.butyl-4-hydroxybenzyl)-2,3,5,6-tetramethylbenzene and 2,4,6-tri-(3,5-di-tert.butyl-4-hydroxybenzyl)-phenol.

1.8. s-Triazine compounds, such as, for example, 2,4-bis-octylmercapto-6-(3,5-di-tert.butyl-4-hydroxyanilino)-s-triazine, 2-octylmercapto-4,6-bis-(3,5-di-tert.butyl-4-hydroxyanilino)-s-triazine, 2-octylmercapto-4,6-bis-(3,5-di-tert.butyl-4-hydroxy-phenoxy)-s-triazine, 2,4,6-tris-(3,5-di-tert.butyl-4-hydroxy-phenoxy)-s-triazine, 2,4,6-tris-(3,5-di-tert.butyl-4-hydroxyphenylethyl)-s-triazine and 1,3,5-tris-(3,5-di-tert.butyl-4-hydroxybenzyl)-isocyanurate.

1.9. Amides of β-(3,5-di-tert.butyl-4-hydroxyphenyl)-propionic acid, such as, for example, 1,3,5-tris-(3,5-di-tert.burtyl-4-hydroxyphenyl-propionyl)-hexahydro-s-triazine and N,N'-di-(3,5-di-tert.butyl-4-hydroxyphenyl-propionyl)-hexamethylenediamine. 1.10. Esters of β-(3,5-di-tert.butyl-4-hydroxyphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]-octane.

1.11. Esters of β-(5-tert.butyl-4-hydroxy-3-methylphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thia-pentadecanol, trimethylhexanediol, trimethylolethane, trimethylolpropane, trishydroxyethyl isocyanurate and 4-hydroxymethyl-1-phospha-2,6,7-trioxabicyclo-[2,2,2]-octane.

1.12. Esters of 3,5-di-tert.butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thio-diethylene glycol, neopentyl glycol, pentaerythritol, 3-thiaundecanol, 3-thia-pentadecanol, trimethylhexanediol, trimethylolethane, trimethylolpropane, trishydroxyethyl isocyanurate and 4-hydroxymethyl-1-phospha-2,6,7-trioxabicyclo-[2,2,2]-octane.

1.13. Benzylphosphonates, such as, for example, 3,5-di-tert.butyl-4-hydroxybenzyl-phosphonic acid dimethyl ester, 3,5-di-tert.butyl-4-hydroxybenzyl-phosphonic acid diethyl ester, 3,5-di-tert.-butyl-4-hydroxybenzyl-phosphonic acid dioctadecyl ester and 5-tert.butyl-4-hydroxy-3-methylbenzyl-phosphonic acid dioctadecyl ester.

Illustrative examples of phosphites are:
Tris-(nonylphenyl)phosphite
tri-butylphosphite
tri-octadecyl phosphite
distearylphentaerythritol diphosphite
tris (2,4 -di-tert.butyl phenyl)phosphite
phenyldiisodedecyl phosphite
diphenyl isodecyl phosphite
bis-(2,4 di-tert.butyl phenyl)pentaerythritol diphosphite Thiosynergists that can be employed can be represented by the formula $$\begin{array}{c} \text{O} \\ \text{R—O—C—}(C_mH_{2m})\text{—CH}_2 \\ \phantom{\text{R—O—C—}(C_mH_{2m})\text{—CH}}| \\ \phantom{\text{R—O—}}\text{O}\phantom{(C_mH_{2m})\text{—CH}}\text{S} \\ \phantom{\text{R—O—}}\| \phantom{(C_mH_{2m})\text{—CH}}| \\ \text{R—O—C—}(C_mH_{2m})\text{—CH}_2 \end{array}$$

wherein R is an alkyl group having from 6 to 24 carbon atoms; and m is an integer from 1 to 6. Especially useful co-stabilizers are dilauryl-β-thiodipropionate and distearyl-β-thiodipropionate tetrakis[methylene-2-dodecylthiopropionate]methane dimeristylthiodipropionate Illustrative examples of metal deactivators are
N,N'-disalicylidineoxaldihydrazide
N,N'-dinaphthoylhydrazine
N,N'-bis(2-hydroxynaphthoyl)hydrazine
N,N'-bis(2-hydroxybenzoyl)-2,2-thio-bis(propionylhydrazine)
N,N'-bis-(2-hydroxybenzoyl)hydrazine
3-(2-hydroxybenzamido)-1,2,4-triazole
N,N'-diacetyladipic acid dihydrazide
N,N'-dibenzoyl sebacicacid dihydrazide
N,N'-bis(3,5-tert.butyl-4-hydroxybenzoyl)hydrazine Illustrative examples of crosslinking agents are
dicumyl peroxide
α,α'-Bis(t-butylperoxy) diisopropyl benzene
di-t-butyl peroxide
2,5-Dimethyl-2,5-bis(t-butylperoxy)hexane
2,5-Dimethyl-2,5-bis(t-butylperoxy)benzyne-3
benzoylperoxide
bis(2,4-dichlorobenzoyl)peroxide
bis-p-chlorobenzoyl peroxide
t-butylperoxy isopropyl carbonate
bis-(4-t-butylcyclohexyl)peroxycarbonate
t-butyl peroxymaleic acid
1,1-di-t-butylperoxy-3,3,5-trimethyl cyclohexane
n-butyl-4,4-bis(t-butylperoxy)valerate Illustrative examples of the polyalkylthiobenzenes particularly useful in stabilizing polymeric materials are:
1. 1,4-di-n-octylthiobenzene
2. 1,4-di-n-octadecylthiobenzene
3. 1,2,4-di-tri-n-dodecylthiobenzene
4. 1,2,4tri-n-tridecylthiobenzene
5. 1,3,5-tri-n-octylthiobenzene
6. 1,3,5-tri-tert-dodecylthiobenzene
7. 1,2,4,5-tetraethylthiobenzene
8. 1,2,4,5-tetra-n-ocytlthiobenzene
9. 1,2,4,5-tetra-n-dodecylthiobenzene
10. 1,2,4,5-tetra-n-tridecylthiobenzene
11. 1,2,3,4,5,6-hexa-n-butylthiobenzene
12. 1,2,3,4,5,6-hexa-n-oddecylthiobenzene
13. 1,2-di-n-octylthio-4-n-octylbenzene
14. 3,5-di-n-dodecylthiotoluene
15. 1,3,5-tri-n-butyl-2,4,6-tri-n-butylthiobenzene To illustrate further the present invention there are provided below examples of the stabilization of a number of substrates. These examples are presented for illustration purposes and should not be used in limiting the scope of this invention.

EXAMPLE 1

Stabilization of Mineral Oil

The compounds listed in the Table I below have been subjected to the Sligh Oil Oxidation Test which measures the uptake of oxygen. It involves heating 10 g. of Primol 355 mineral oil (sold by EXXON) containing 0.1% of a stabilizer at 150° C. in an atmosphere of oxygen. The time of failure is measured manometrically as the time it takes for the pressure to drop 15 cm. of Hg. The stabilizer numbers in the Table refer to the numbered list of polyalkylthiobenzenes which appear above.

TABLE I

SLIGH OIL OXIDIATION TEST

| Stabilizer | Time to Failure |
| --- | --- |
| No. 1 | 30.6 hrs. |
| No. 5 | 79.1 |
| No. 11 | 53.2 |
| No. 8 | 37.1 |
| No. 7 | 71.3 |
| Unstabilized | 2.0 |

EXAMPLE 2

Stabilization of Turbine Oil

In the Staeger Oil Test a stabilizer (0.5%) is dissolved in 170 g. of EXXON mineral Turbine Oil 1243 which is then oven aged at 110° C. The failure time is determined when the change in the acid number becomes greater than 0.2 meq. KOH/g oil as determined by potentiometric titration of an aliquot of the aged oil with standard 0.05 M alcoholic KOH after the addition of titration solvent. The stabilizer numbers in Table II below refer to the numbered stabilizers listed supra.

TABLE II

Staeger Oil Test

| Stabilizer | Time to Failure |
| --- | --- |
| No. 5 | 750 hrs. |
| No. 11 | 680 hrs. |
| No. 8 | 650 hrs. |
| Unstabilized | 370 hrs. |

EXAMPLE 3

Stabilization of Crosslinked Polyethylene

A stabilizer is incorporated into low density polyethylene resin by milling the resin/stabilizer blend at 216° F. (102° C.) for 4 minutes. After 4 minutes milling 2% dicumyl peroxide was added and milling was continued for an additional 3 minutes.

The milled resin was cured into 65 mil thick plaques using two curing cycles; first, 10 minutes at 248° F. (120° C.) and second, 15 minutes at 350° F. (177° C.), after which dumbbell shaped microtensile specimens were die cut. The specimens were oven aged at 150° C. and periodically tested on an Instron Model TM for tensile strength (psi-pounds per square inch) and percent (%) elongation.

TABLE III

CROSSLINKED POLYETHYLENE STABILIZATION

| | Initial | | % Retention after Weeks of Aging | | | | | | | |
|---|---|---|---|---|---|---|---|---|---|---|
| | TS | | 2 | | 4 | | 6 | | 8 | |
| Stabilizer | psi | E | TS | E | TS | E | B | E | TS | E |
| (1) Unstabilized | Failed in one day | | | | | | | | | |
| (2) 0.2% Santonox R[1] | 2730 | 640 | 26 | 8 | | | | | | |
| (3) 0.2% Santonox R + 0.3% DSTDP | 2790 | 690 | 63 | 62 | 31 | 10 | | | | |
| (4) 0.5% Age Rite Resin D[2] | 2900 | 700 | 66 | 84 | 68 | 73 | 14 | 7 | | |
| (5) 0.2% Flectol H[3] | 2750 | 600 | 20 | 10 | | | | | | |
| (6) 0.1% No. 8 | 2190 | 590 | 85 | 58 | 56 | 41 | 59 | 49 | 63 | 33 |
| (7) 0.2% No. 8 | 2190 | 610 | 70 | 65 | 69 | 58 | 64 | 52 | 67 | 50 |
| (8) 0.2% Santonox R 0.1% No. 8 | 2260 | 630 | 99 | 94 | 90 | 83 | 76 | 72 | 74 | 58 |
| (9) 0.2% AO-1[4] 0.1% No. 8 | 2250 | 610 | 92 | 90 | 86 | 81 | 77 | 75 | 52 | 10 |
| (10) 0.2% AO-2[5] 0.1% No. 8 | 2300 | 620 | 95 | 90 | 74 | 70 | 62 | 45 | 56 | 30 |
| (11) 0.2% AO-3[6] 0.1% No. 8 | 2120 | 580 | 87 | 74 | 96 | 89 | 84 | 78 | 88 | 69 |
| (12) 0.2% AO-4[7] 0.1% No. 8 | 2330 | 640 | 91 | 86 | 72 | 63 | 70 | 68 | 51 | 11 |
| (13) 0.2% AO-5[8] 0.1% No. 8 | 2220 | 630 | 100 | 91 | 85 | 70 | 72 | 70 | 58 | 17 |
| (14) 0.2% AO-6[9] 0.1% No. 8 | 2240 | 620 | 70 | 69 | 62 | 57 | 51 | 33 | 59 | 21 |
| (15) 0.2% AO-7[10] 0.1% No. 8 | 2320 | 620 | 94 | 89 | 86 | 83 | 49 | 16 | 49 | 9 |
| (16) 0.2% No. 3 | 2250 | 550 | 74 | 70 | 67 | 62 | 61 | 47 | 59 | 52 |
| (17) 0.1% AO-5 0.1% No. 3 | 2350 | 570 | 84 | 78 | 78 | 69 | 45 | 13 | 36 | 7 |
| (18) 0.2% No. 9 | 2490 | 590 | 73 | 73 | 61 | 58 | 50 | 32 | 50 | 37 |
| (19) 0.1% AO-5 | 2240 | 560 | 92 | 83 | 69 | 61 | 51 | 24 | 45 | 17 |
| (20) 0.2% No. 5 | 2380 | 570 | 79 | 71 | 69 | 61 | 66 | 50 | 60 | 45 |
| (21) 0.1% AO-5 0.1% No. 5 | 2230 | 550 | 91 | 91 | 87 | 84 | 76 | 58 | 69 | 66 |

Notes on Table III
The horizontal lines in the above Table separate different testing series carried out at different times.
[1]Santonox R is 4,4'-thio-bis(6-t-butyl-m-cresol)
[2]Age Rite Resin D (Vanderbilt) is a polymeric 2,2,4-trimethyl-1,2-dihydroquinoline
[3]Flectol H (Monsanto) is a polymeric 2,2,4-tri-methyl-1,2-dihydroquinoline
[4]AO-1 is 1,6-hexamethylene bis-(3,5-di-t-butyl-4-hydroxyhydrocinnamate)
[5]AO-2 is 2,4-bis-(n-octylthio)-6-(3,5-di-t-butyl-4-hydroxyanilino-1,3,5-triazine
[6]AO-3 is thiodiethylene bis-(3,5-di-t-butyl-4-hydroxyhydrocinnamate)
[7]AO-4 is neopentane glycol-bis[3-(3,5-di-t-butyl-4-hydroxyphenyl)propionate]
[8]AO-5 is octadecyl β-(3,5-di-t-butyl-4-hydroxyphenyl)propionate
[9]AO-6 is dioctadecyl 3,5-di-t-butyl-4-hydroxybenzylphosphonate
[10]AO-7 is N,N'-hexamethylene bis (3,5-di-t-butyl-4-hydroxyhydrocinnamamide)

EXAMPLE 4

Exudation from Uncrosslinked Polyethylene

The stabilizer is incorporated in the same manner as described in Example 3. The milled resin was compression molded into 4 in. × 4 in. × 0.65 in (10.16 cm × 10.16 cm × 1.65 cm) plaques at 248° F. (120° C.) for 7 min. (2% of dicumyl peroxide was also incorporated but crosslinking does not take place during the compression molding operation). The specimens were oven aged at room temperature and at 60° C. and periodically examined visually to determine the degree of exudation of the stabilizer which exhibits itself as a powdery material on the surface of the specimen. The degree of exudation was rated as follows: 0 (no visible exudation), 1 (slightly visible), 2 (easily visible), 3 (tiny crystals evident) and 4 (heavy coating).

When polyethylene plaques containing 0.1% and 0.2% of Compound No. 8 were tested as described above, they were rated 0 after 5 days at room temperature, 1 at room temperature up to 60 days and 1 up to 40 days at 60° C.

When polyalkylthiobenzenes are used in combination with phenolic antroxidants which are compatible with the substrate, a composition is obtained which has superior retention of physical properties and freedom from exudation. The most preferred antioxidant is octadecyl β-(3,5-di-t-butyl-4-hydroxyphenyl) propionate.

EXAMPLE 5

Exudation from Uncrosslinked Polyethylene

The procedure described in Example 4 was followed in preparing the specimen. The exudation tests were also carried out as described in Example 4 at the temperatures indicated in Table IV below.

TABLE IV

| Exudation from Uncrosslinked Polyethylene | | | | | |
|---|---|---|---|---|---|
| | | 0.2% of Compound No. | | | |
| Days | Temp. | 3 | 5 | 8 | 9 |
| 4 | 25° C. | 0 | 0 | 0 | 0 |
| | 60 | 0 | 0 | 0 | 0 |
| 8 | 25 | 0 | 0 | 0 | 0 |
| | 60 | 0 | 1 | 0 | 0 |
| 15 | 25 | 1 | 0 | 0 | 1 |
| | 60 | 0 | 0 | 0 | 0 |
| 26 | 25 | 1 | 0 | 0 | 1 |
| | 60 | 0 | 1 | 0 | 0 |
| 41 | 25 | 1 | 0 | 0 | 2 |
| | 60 | 0 | 0 | 0 | 0 |

EXAMPLE 6

Stabilization of Carbon Black Loaded Crosslinked Polyethylene

900 Parts of low density polyethylene (Union Carbide DYNH-1) and 360 parts of Vanderbilt MT carbon black (particle size 330 ± 50 μm) were placed into a Banbury mixer and mixed slowly using speed 2 with cooling water running. The composition was mixed for about 2 min. by which time the temperature reached 230°–240° F. (110°–115° C.). The mixture was removed from the Banbury mixer and the resulting material was sheeted on a cold two-roll mill.

The sheeted material was then milled again incorporating the stabilizer and dicumyl peroxide following the procedure described in Example 3. The 65 mil plaques were then tested for tensile strength and percent elongation as described in Example 3. The data is presented in Table V below.

TABLE V
Crosslinked Carbon Black Loaded Polyethylene Stabilization

| | Initial | | % Retention After Weeks of Aging | | | | | | | |
|---|---|---|---|---|---|---|---|---|---|---|
| | TS | | 2 | | 4 | | 6 | | 8 | |
| Stabilizer | Psi | E | TS | E | TS | E | TS | E | TS | E |
| (1) No Stabilizer | 2190 | 430 | 28 | 6 | Failed | | | | | |
| (2) 0.1% No. 8 | 2230 | 440 | 108 | 86 | 101 | 74 | 95 | 68 | 91 | 58 |
| (3) 0.2% No. 8 | 2230 | 400 | 112 | 90 | 110 | 93 | 101 | 75 | 101 | 67 |
| (4) 0.2% No. 3 | 2270 | 400 | 109 | 87 | 110 | 82 | 107 | 74 | 103 | 59 |
| (5) 0.2% No. 9 | 2300 | 440 | 107 | 79 | 105 | 73 | 100 | 61 | 96 | 56 |
| (6) 0.1% No. 8 + 0.2% AO-1[1] | 2220 | 410 | 112 | 94 | 110 | 85 | 99 | 73 | 102 | 65 |
| (7) 0.1% No. 8 + 0.2% AO-8[2] | 2330 | 410 | 108 | 85 | 106 | 81 | 104 | 76 | 102 | 68 |
| (8) 0.1% No. 8 + 0.2% AO-3 | 2220 | 420 | 107 | 90 | 107 | 83 | 102 | 71 | 100 | 65 |
| (9) 0.1% No. 8 + 0.2% AO-2 | 2390 | 440 | 99 | 81 | 99 | 76 | 92 | 66 | 82 | 53 |
| (10) 0.1% No. 8 + 0.2% AO-5 | 2280 | 440 | 108 | 89 | 109 | 94 | 99 | 68 | 98 | 64 |
| (11) 0.075% No. 8 + 0.075% AO-5 | 2220 | 430 | 104 | 83 | 100 | 83 | 93 | 62 | 85 | 50 |
| (12) 0.1% No. 3 + 0.1% AO-5 | 2230 | 410 | 106 | 90 | 104 | 80 | 101 | 71 | 93 | 62 |
| (13) 0.1% No. 9 + 0.1% AO-5 | 2220 | 430 | 110 | 83 | 113 | 84 | 94 | 68 | 99 | 61 |
| (14) 0.1% No. 6 + 0.1% AO-5 | 2260 | 410 | 101 | 85 | 95 | 67 | 89 | 58 | 80 | 34 |

[1]See identification of various antioxidants (AO) in the Note to Table III.
[2]AO-8 is pentaerithritol tetrakis -[3-(3',5'-di-t-butyl-4'-hydroxyphenyl) propionate]

EXAMPLE 7

Oven Aging of Polypropylene

Unstabilized polypropylene powder (Hercules Profax 6501) was thoroughly blended with 0.3% by weight of the indicate stabilizer compound. Also prepared were samples of polypropylene containing 0.3% by weight of the same stabilizer and 0.1% be weight of AO-8 which is identified in Table V. The blended materials were then milled on a two-roll mill at 182° C. for 10 minutes after which time the stabilized polypropylene was sheeted from the mill and allowed to cool.

The milled polypropylene sheets were then cut into pieces and pressed for 7 minutes on a hydraulic press at 218° C. and 275 psi (19.25 Kg/cm²) pressure. The resulting plaques of 25 mil (0.635 mm) thickness were tested for resistance to accelerated aging in a forced draft oven at 150° C. A corner of the test specimen was flared 180°. The specimen is considered to have failed if after the flaring the specimen becomes embrittled which leads to cracking. The data is presented in Table VI below.

TABLE VI

| Stabilizer | Failure Time |
|---|---|
| 0.3% No. 3 | 160 hours. |
| 0.3% No. 3 + 0.1% AO-8 | 680 hours. |
| 0.3% No. 9 | 160 hours. |
| 0.3% No. 9 + 0.1% AO-8 | 680 hours. |
| 0.3% No. 8 | 210 hours. |
| 0.3% No. 8 + 0.1% AO-8 | 680 hours. |
| Without Stabilizer | 3 hours. |

What is claimed is:

1. A method of stabilizing organic material subject to oxidative deterioration by incorporating therein 0.01 to 5% of a stabilizer having the formula

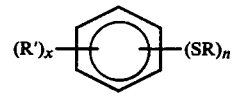

wherein
R is an alkyl group of 1 to 24 carbon atoms, a cycloalkyl group of 4 to 7 carbon atoms or an alkylcycloalkyl group of 7 to 30 carbon atoms,
R' is an alkyl group of 1 to 18 carbon atoms,
n is an integer from 2 to 6
x is an integer from 0 to 4 provided that n + x is not greater than 6.

2. A method of claim 1 wherein said organic material is selected from an olefinic polymer, chlorinated polyolefin, a diene rubber and lubricating oil.

3. A method of claim 2
wherein
R is alkyl of 2 to 18 carbon atoms,
R' is alkyl of 1 to 8 carbons,
n is 2 to 4 and
x is 0 to 2.

4. A method of claim 3 wherein x is 0.

5. A method of claim 4 wherein the polymeric material is polyethylene.

6. A method of claim 5 wherein the stabilizer is 1,2,4,5-tetra-n-octylthiobenzene.

7. A method of claim 3 wherein the organic material is lubricating oil.

8. A method of claim 1 containing additionally a phenolic antioxidant.

9. A method of claim 8 wherein the phenolic antioxidant is selected from the group consisting of pentaerythritol tetrakis-[3-(3′,5′-di-tert-butyl-4′-hydroxyphenyl)-propionate] dioctadecyl 3,5-di-tert-butyl-4-hydroxybenzyl phosphonate N,N′-hexamethylene bis (3,5-di-tert-butyl-4-hydroxyhydrocinnamide) octadecyl β-(3,5-di-tert-butyl-4-hydroxphenyl)propionate thiodiglycol bis-(3,5-di-tert-butyl-4-hydroxyphenyl)propionate 2,4-bis-(n-octylthio)-6-(3,5-di-tert-butyl-4-hydroxyanilino)-1,3,5-triazine 1,6-hexamethylene bis-(3,5-di-tert-butyl-4-hydroxyhydrocinnamate) 1,3,5-tris(3,5-di-t-4-hydroxybenzyl)isocyanurate 1,1,3-tris(5-tert-butyl-4-hydroxy-2-methyl phenyl)-butane 10. A composition of matter comprising an organic material subject to oxidative deterioration and 0.01% to 5% of a stabilizer having the formula

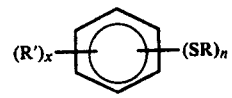

wherein
R is an alkyl group of 1 to 24 carbon atoms, a cycloalkyl group of 4 to 7 carbon atoms or an alkylcycloalkyl group of 7 to 30 carbon atoms,
R′ is an alkyl group of 1 to 18 carbon atoms,
n is a integer from 2 to 6
x is an integer from 0 to 4 provided that n + x is not greater than 6.